United States Patent [19]

Matsukura et al.

[11] Patent Number: 4,981,846

[45] Date of Patent: Jan. 1, 1991

[54] CRYSTALLINE L-CARNOSINE ZINC COMPLEX HAVING ANTIULCER ACTIVITY

[75] Inventors: Takefumi Matsukura, Minamikawachi; Tamiko Takahashi, Minoo; Yasuhiro Nishimura, Fujiidera; Masahiro Takaya, Yasu; Hajime Fujimura, Kyoto, all of Japan

[73] Assignee: Hamari Chemicals, Ltd., Osaka, Japan

[21] Appl. No.: 221,749

[22] Filed: Jul. 20, 1988

[30] Foreign Application Priority Data

Aug. 10, 1987 [JP] Japan .................................. 62-200698

[51] Int. Cl.$^5$ ...................... A61K 31/555; C07F 3/06; C07D 223/64
[52] U.S. Cl. .................................... 514/184; 548/101; 548/104
[58] Field of Search ................. 548/101, 104; 514/184

[56] References Cited

FOREIGN PATENT DOCUMENTS

0192317 8/1986 European Pat. Off. ............ 514/184
0033720 2/1984 Japan .................................. 548/104

OTHER PUBLICATIONS

Weitzel et al., Hoppe-S-Z. Physiol. Chem., 307, 23, (1957).

*Primary Examiner*—Diana G. Rivers
*Attorney, Agent, or Firm*—Burgess, Ryan & Wayne

[57] ABSTRACT

A novel crystalline L-carnosine zinc complex is produced by reacting L-carnosine, a zinc salt and an alkali metal compound in an anhydrous or hydrous polar organic solvent.

The crystalline L-carnosine zinc complex substantially corresponds to the formula $C_9H_{12}N_4O_3Zn$ and has physical properties clearly different from the known amorphous L-carnosine zinc complex.

As compared with the amorphous complex, the crystalline complex is very low in impurity, stable to heat and moisture, and easy to filtrate, and has higher anti-ulcer activity.

3 Claims, 9 Drawing Sheets

CRYSTALLINE L-CARNOSINE ZINC COMPLEX HAVING ANTIULCER ACTIVITY

The present invention relates to a crystalline L-carnosine zinc complex having the composition of $C_9H_{12}N_4O_3Zn$ and a method of producing the same.

It is known, as mentioned in Japanese Unexamined Patent Application Kokai No. 59-33270, that the L-carnosine zinc complex has the property to protect the mucosa and repair impaired tissues and is, therefore, an excellent therapeutic agent for peptic ulcers causing a minimum of adverse reaction. However, when the L-carnosine zinc complex is prepared in water by the conventional method described in Japanese Unexamined Patent Application No. 59-33270 or by the method proposed by Weitzel and his colleagues (G. Weitzel et al., Hoppe-S-Z. Physiol. Chem., 307, 23 (1957), the resulting complex is usually a mixture of various zinc chelate compounds showing diffuse IR, far infrared and NMR spectra. This complex is an amorphous substance, showing no defined powder X-ray diffraction pattern. Thus, the substance cannot be identified as a single chemical entity and so labile to heat and moisture that it cannot be used as a reliable medicament. Furthermore, in the manufacturing process, a long time is required for filtration, with the resultant decrease in workability, and moreover, considerable difficulties are involved in the removal of impurities such as inorganic ions.

In the course of research for the development of a commercial process for production of a L-carnosine zinc complex, the present inventors found that conducting the complex-forming reaction under a specified set of conditions yielded a crystallline L-carnosine zinc complex which was completely different in physicochemical entity from the amorphous L-carnosine zinc complex that is obtained by the conventional production method. This crystalline L-carnosine zinc complex is a novel substance. Thus, the present inventors found that when the reaction is conducted using 0.8 to 1.2 moles of a zinc salt and 1.6 to 2.4 moles of an alkali metal compound to each mole of L-carnosine in an anhydrous or hydrous polar organic solvent either at room temperature or at an elevated temperature, there is obtained an L-carnosine zinc complex which is crystalline, has a single composition, is stable against heat and moisture, lends itself well to filtration, is easy to purify, and has an improved efficacy. The present invention is predicated on the above findings.

Thus, the present invention relates to a crystalline L-carnosine zinc complex giving an elemental analysis substantially conforming to the formula $C_9H_{12}N_4O_3Zn$ and a process for producing a crystalline L-carnosine zinc complex which comprises reacting L-carnosine, a zinc salt and an alkali metal compound in an anhydrous or hydrous polar organic solvent.

The polar organic solvent used in the production of a crystalline L-carnosine zinc comples according to the invention is exemplified by alcohols such as methanol, ethanol, propanol, etc., acetonitrile, dimethyl sulfoxide, N,N-dimethylformamide, tetrahydrofuran, acetone, and so on. These solvents may contain up to about 50 percent of water. The alkali metal compound may for example be lithium hydroxide, potassium hydroxide, sodium hydroxide, potassium alkoxide or sodium alkoxide. These are not exclusive choices but any other alkali metal compound that permits the reaction to proceed can also be utilized. The zinc salt may be whichever of inorganic and organic salts. As examples of the inorganic salt, there may be mentioned zinc halide, zince sulfate, zinc nitrate and zinc perchlorate, while the organic salt may be a salt of zinc with a carboxylic acid, such as zinc acetate, zinc acetylacetonate, or the like. These are only illustrative and any zinc salt that will not interfere with the progress of the reaction can be employed.

The preferred proportions of these reactants are 0.8 to 1.2 moles of zinc salt and 1.6 to 2.4 moles of alkali metal compound relative to each mole of L-carnosine.

While the reaction is conducted either at an elevated temperature or at room temperature, the reaction generally proceeds satisfactorily and fast enough at room temperature.

The crystalline L-carnosine zinc complex thus obtained has excellent properties as a drug and can be administered generally orally or otherwise, either as it is or as formulated with an appropriate vehicle, carrier or diluent. For oral administration, there may be used such dosage forms as powder, tablets, pills, capsules, granules, and so on. The dosage forms for administration by routes other than oral include suppositories, injections, drips, and so on. The daily oral dose for adult humans is generally 10 mg to several grams and preferably 20 mg to 1 gram. The dosage may be adjusted according to the patient's condition. It is also possible that the complex of the invention be administered in combination with other optional drugs.

Referring to FIGS. 1 to 4, A represents the crystalline L-carnosine zinc complex and B represents the amorphous L-carnosine zinc complex.

The description, physical properties and pharmacological effects of the crystalline L-carnosine zinc complex produced by the method of Example 1 are shown below in comparison with those of the amorphous L-carnosine zinc complex produced by the conventional method described in Reference Example 1.

(1) Color of substance: Both crystalline and amorphous complexes are white or pale yellowish white.

(2) Morphology of substance: Electron micrographs at $\times 10,000$ magnification show that whereas the crystalline complex appears granular, the amorphous complex appears to be large lumps.

(3) Solubility: Both the crystalline complex and the amorphous complex are insoluble in the common organic solvents and water.

(4) Elemental analysis: The CHN Corder MT-3 manufactured by Yanagimoto Seisakusho, Ltd. was used for C, H and N and atomic absorption spectrophotometry was used for Zn.

| (I) Crystalline L-carnosine zinc complex | | |
|---|---|---|
| Element | Calcd. ($C_9H_{12}N_4O_3Zn$) | Found |
| C | 37.33% | 37.07% |
| H | 4.18 | 4.27 |
| N | 19.35 | 19.06 |
| Zn | 22.53 | 22.50 |

| (II) Amorphous L-carnosine zinc complex | |
|---|---|
| Element | Found |

-continued

| | |
|---|---|
| C | 29.57% |
| H | 4.11 |
| N | 15.43 |
| Zn | 20.40 |

It is apparent from the above data that the crystalline L-carnosine zinc complex is a 1:1 complex derived from zinc and L-carnosine on removal of 2 hydrogen atoms from the latter.

Figure 1A:
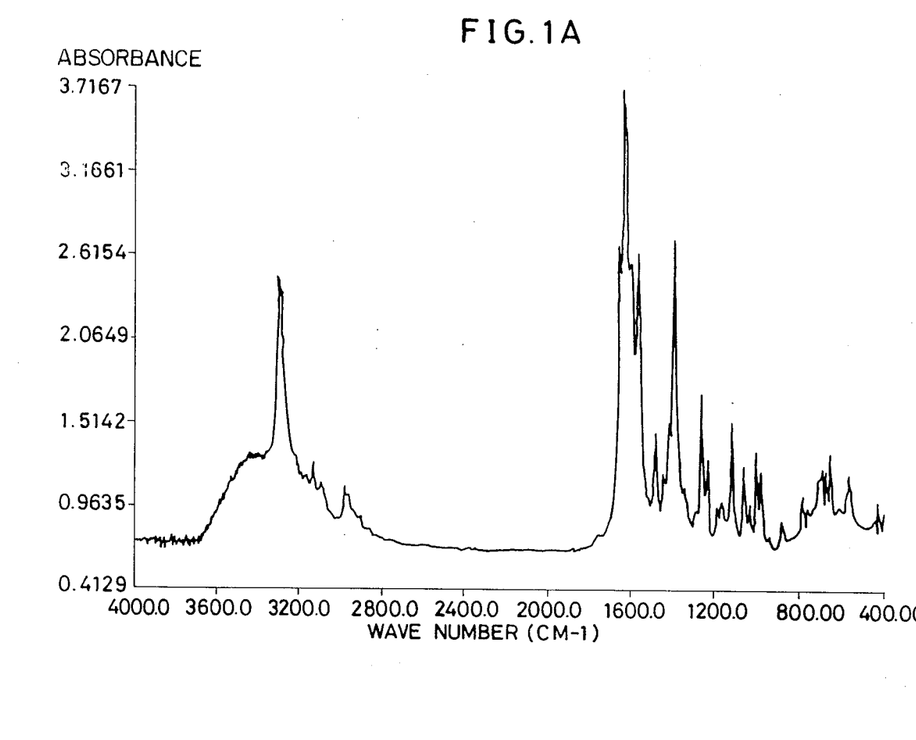
FIG. 1 shows the infrared absorption spectra.
Figure 1B:
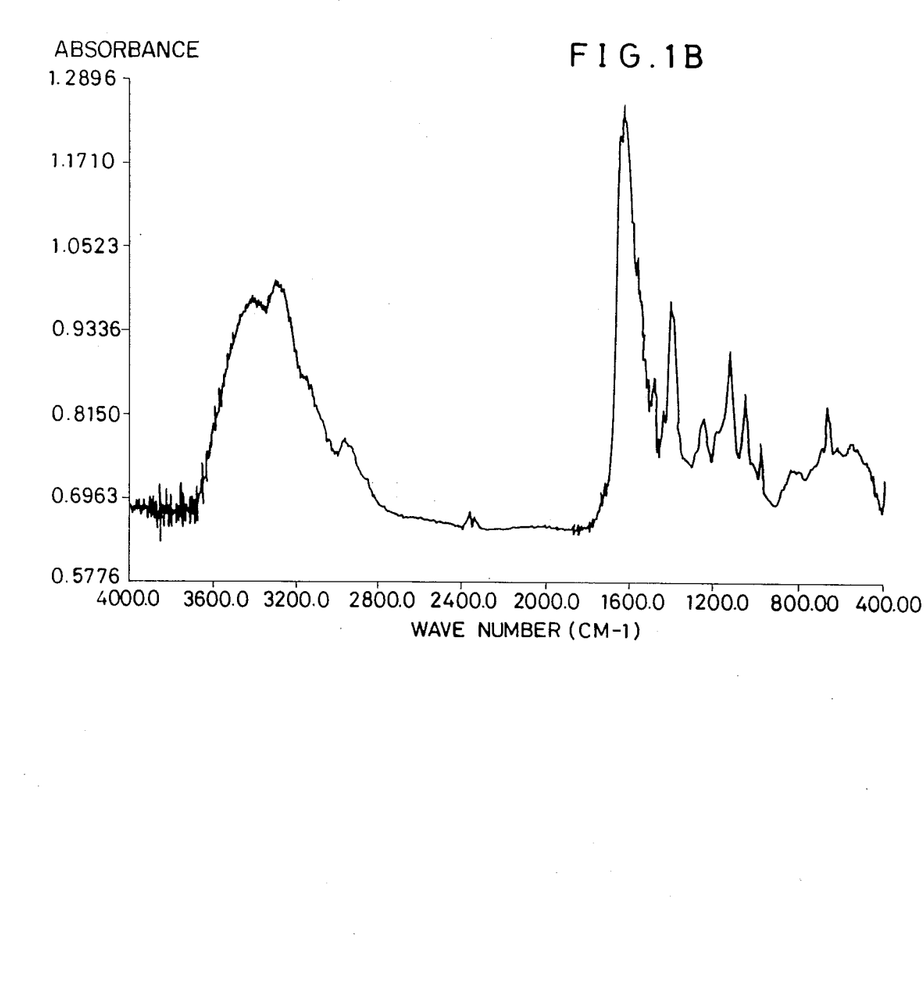

(5) Infrared absorption spectrum: The IR spectrum (KBr) determined by means of Nicolet's 5ZDX FT-IR is shown in FIG. 1.

The dominant absorptions of crystalline L-carnosine zinc complex are as follows.

Absorption wavenumbers ($cm^{-1}$): 3292, 1626, 1563, 1389, 1262, 1230, 1117, 1060, 1030, 999, 982, 883 and 787.

In contrast, the spectrum of the amorphous compound shows less absorptions and is broad, indicating at a glance that it is a mixture. Since the crystalline compound and the amorphous compound are thus quite different from each other in absorption pattern, these are different substances.

Figure 2A:
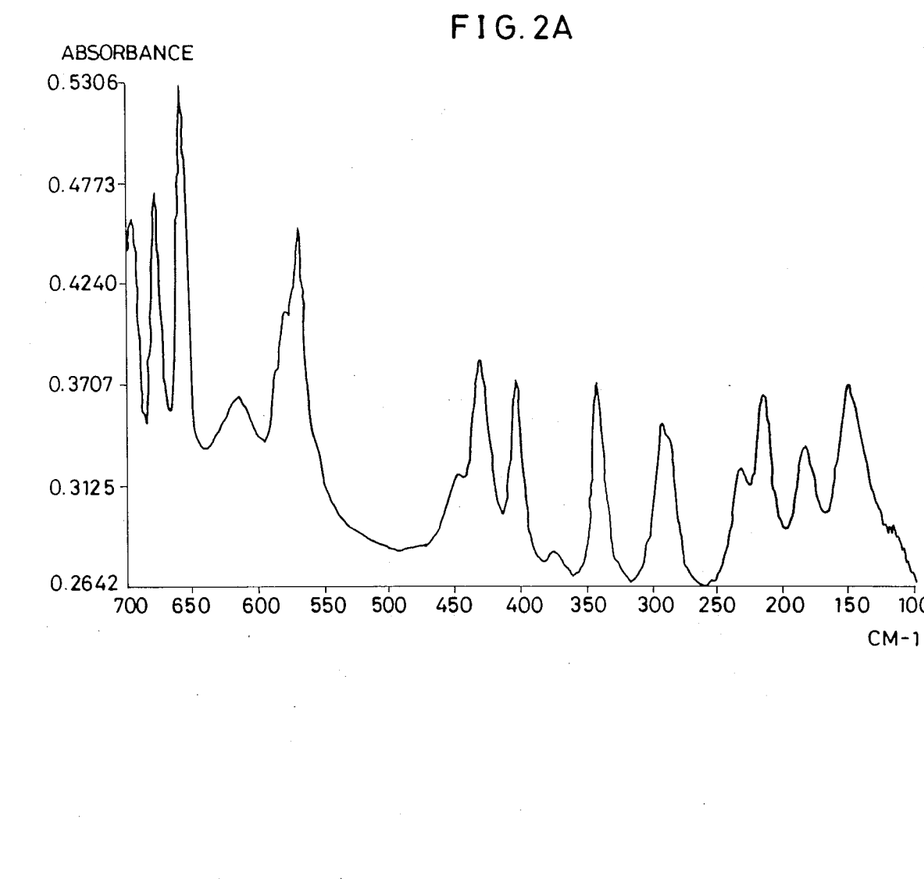
FIG. 2 shows the far infrared absorption spectra.
Figure 2B:
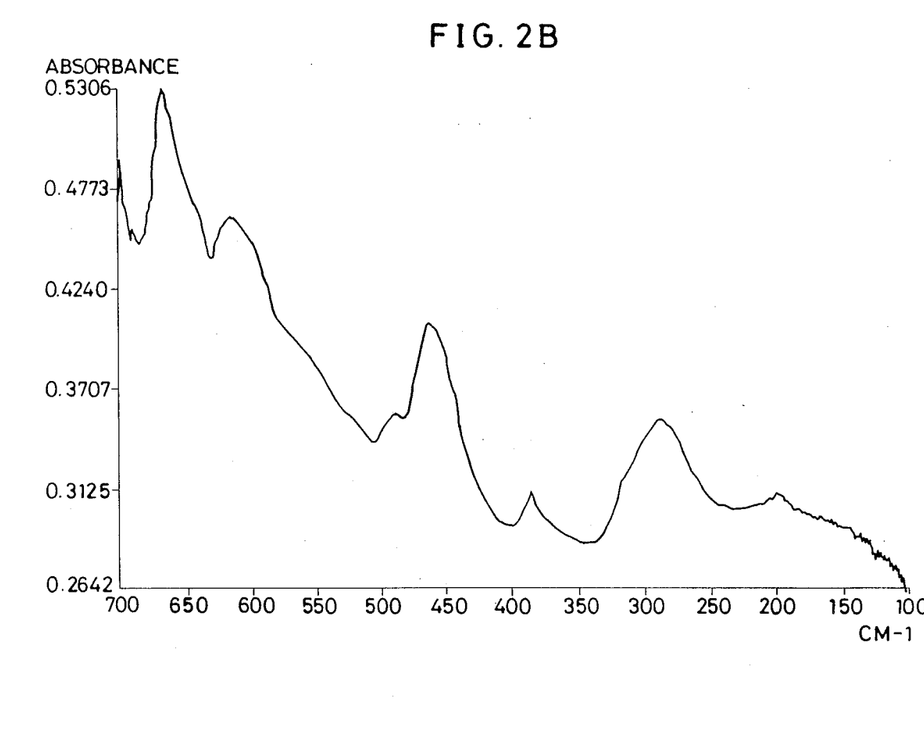

(6) Far infrared absorption spectrum: The far infrared absorption spectrum (Nujol) determined by means of Bruker's IFS-113V FT-IR is shown in FIG. 2.

The crystalline L-carnosine zinc complex showed the absorption wavenumbers ($cm^{-1}$) of 694, 678, 658, 614, 579, 568, 448, 429, 403, 375, 340, 291, 231, 214, 183 and 150.

While the vibration of the zinc-L-carnosine bond appears in the far infrared region of the spectrum, the crystalline compound and the amorphous compound are different in absorption pattern, indicating that these two compounds have different zinc-carnosine bonds. Therefore, they are different substances.

Figure 3A:
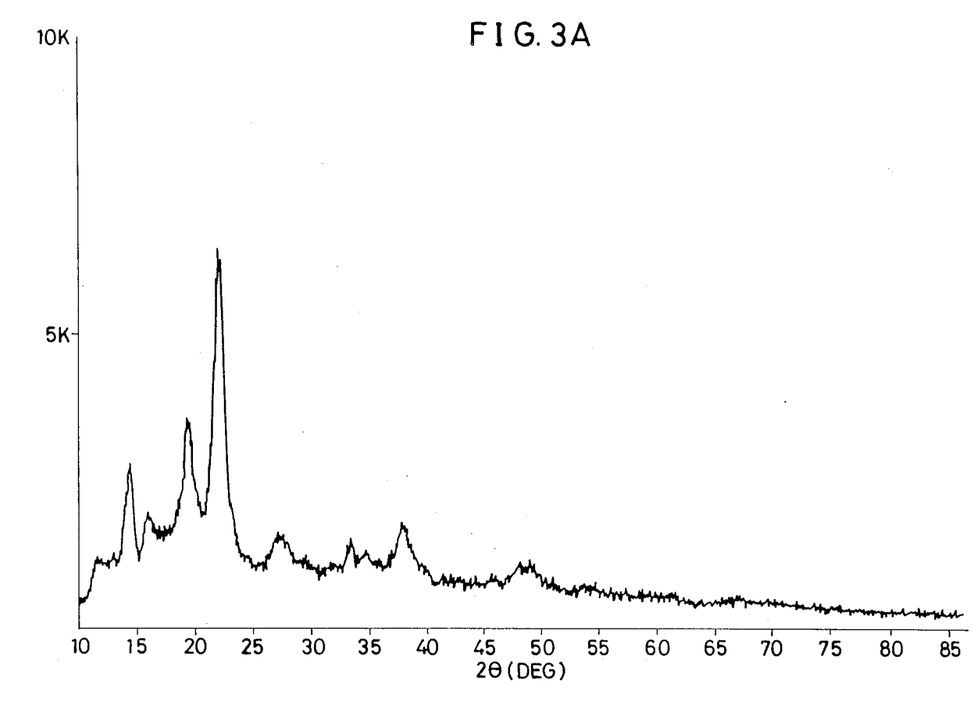
FIG. 3 shows the powder X-ray diffraction spectra.
Figure 3B:
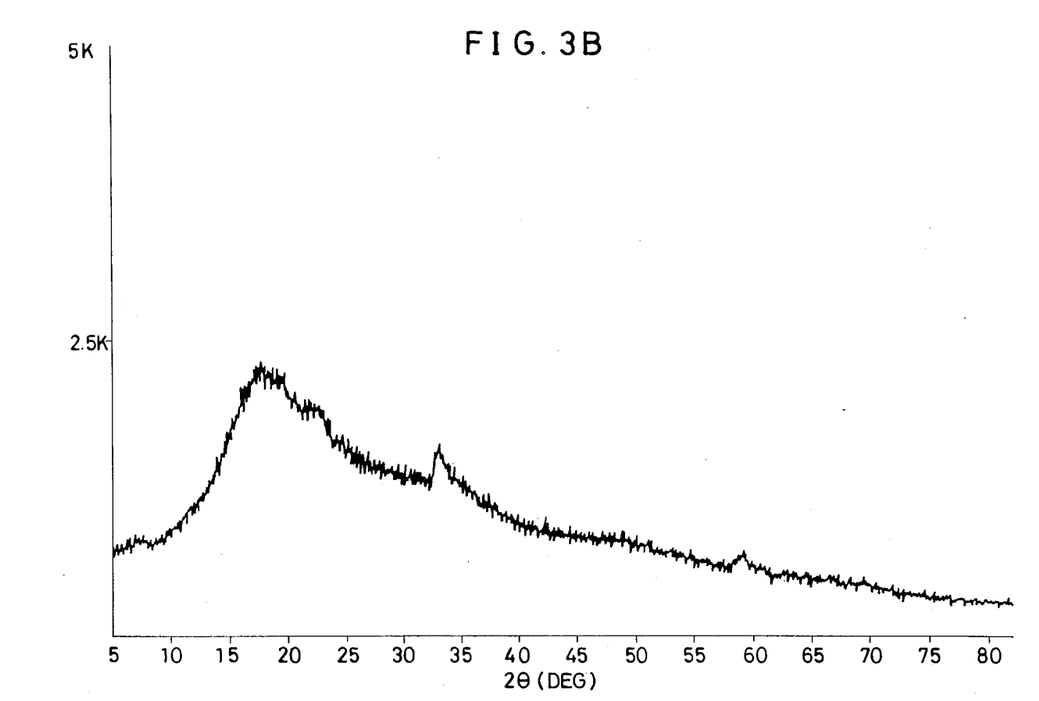

(7) Powder X-ray diffraction analysis: The X-ray diffraction pattern determined by means of Rigaku Denki Ru-200B using the Cu-Ka beam filtered through a nickel filter is shown in FIG. 3.

The diffraction pattern of crystalline L-carnosine zinc complex is shown below.

| Interplanar spacing (d; Å Angstrom unit) | Relative intensity (%, I/Io) |
|---|---|
| 11.87 | 26 |
| 7.54 | 28 |
| 5.97 | 43 |
| 5.55 | 27 |
| 5.26 | 30 |
| 4.52 | 51 |
| 3.96 | 100 |
| 3.56 | 19 |
| 3.24 | 29 |
| 2.97 | 19 |
| 2.79 | 17 |
| 2.68 | 22 |
| 2.58 | 21 |
| 2.38 | 25 |
| 2.10 | 13 |
| 1.97 | 14 |
| 1.88 | 15 |
| 1.84 | 14 |
| 1.69 | 10 |
| 1.57 | 9 |
| 1.55 | 9 |
| 1.53 | 10 |

It is apparent that the crystalline complex has substantially the same degree of crystallinity as ordinary organic compounds. In contrast, the amorphous compound does not give a definite diffraction pattern.

Figure 4A:
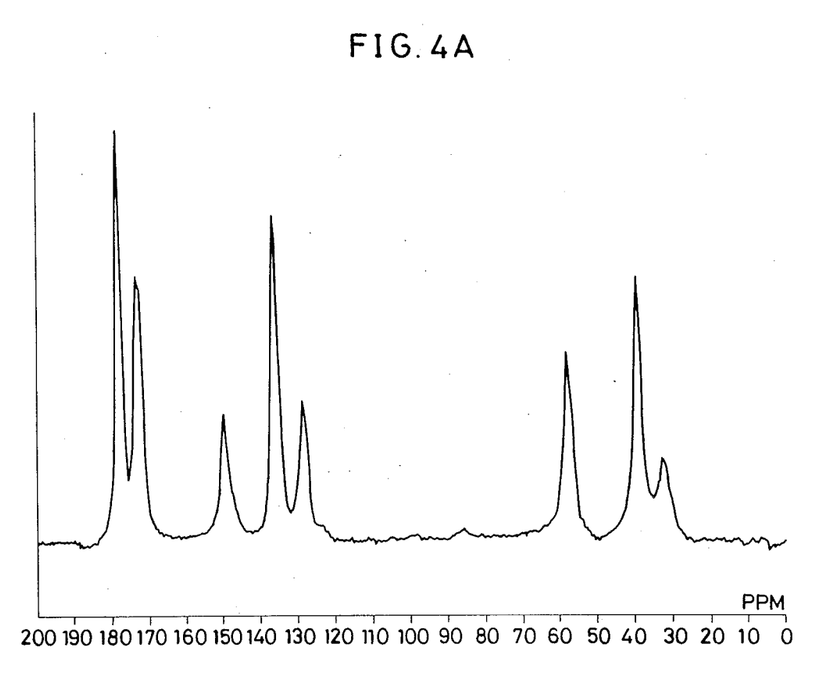
FIG. 4 shows the solid high resolution $^{13}C$-NMR spectra.
Figure 4B:
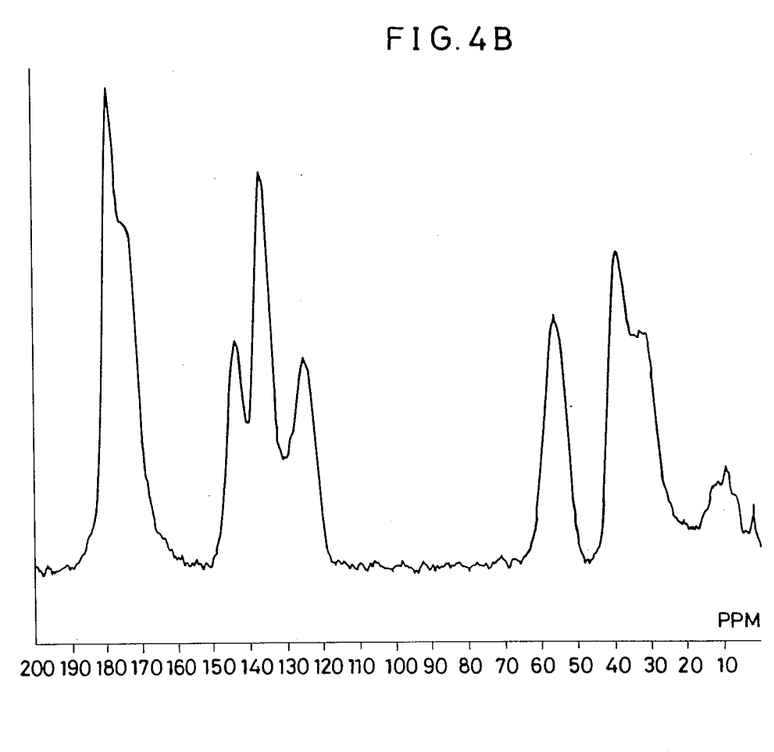

(8) Solid high resolution $^{13}C$-NMR spectrum: The $^{13}C$-CP/MAS-NMR spectrum determined by means of Jeol JNM/GX270 and NM-GSH27M is shown in FIG. 4.

The crystalline L-carnosine zinc complex absorbed at 177.19, 172.52, 149.41, 135.81, 128.04, 57.34, 38.69 and 32.28 ppm (TMS standard), with good resolution, showing no contamination with impurities within the sensitivity limits of NMR. On the other hand, the spectrum of the amorphous product was broad and showed impurity peaks. Moreover, the position of the unsaturated carbon peak was different from that of the crystalline complex. Therefore, the two compounds are different substances.

Figure 5:
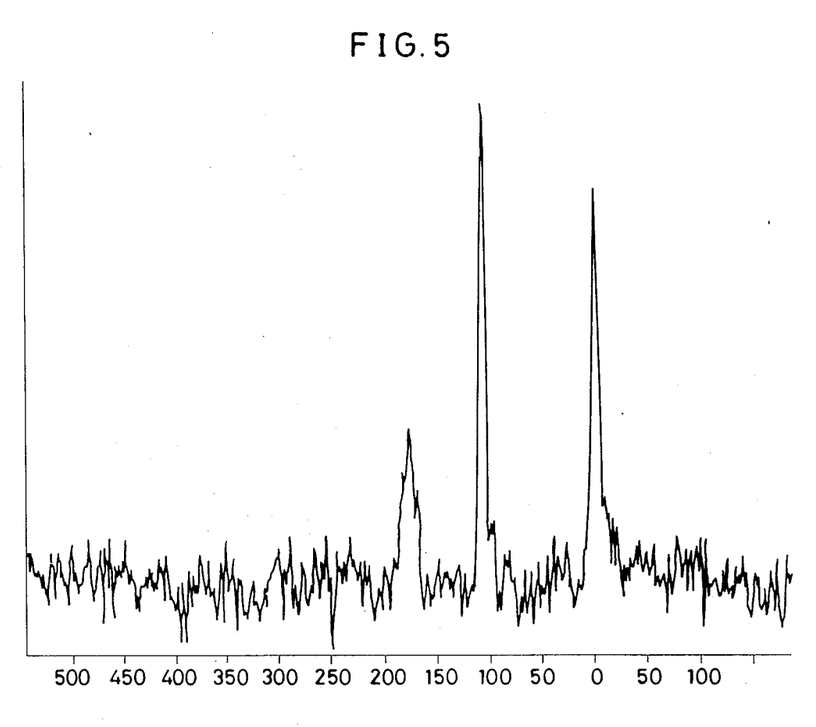
FIG. 5 shows the solid high resolution $^{15}N$-NMR spectrum of the crystalline L-carnosine zinc complex.

(9) Solid high resolution $^{15}N$-NMR spectrum: The $^{15}N$-CP/MAS-NMR spectrum of the crystalline-L-carnosine zinc complex as determined using Jeol JNM-GX270 and NM-GSH27M is shown in FIG. 5. It is apparent that the complex gives absorptions at 177.11, 106.83 and 0.18 ppm ($NH_4NO_3$ standard). The spectrum could not be observed with the amorphous L-carnosine zinc complex.

(10) The amount of impurity: The crystalline and amorphous L-carnosine zinc complex were compared in regard to the amount of impurity.
 (i) Na ion
  Crystalline: 33 ppm
  Amorphous: 18,000 ppm
 (ii) The amount of insoluble impurity in 1N-NaOH was determined.
  Absorbance $A_{650\ nm}$, Concentration 2.44%
  Crystalline: 0.003
  Amorphous: 0.006

It will be apparent that the crystalline L-carnosine zinc complex is very lean in impurity.

(11) Stability: The crystalline and amorphous L-carnosine zinc complexes were stored in an environment of 75% relative humidity at 40° C. for 14 days. Each of the samples was dissolved in 1N-NaOH (concentration 20%) and the degreee of coloration and the change of turbidity were investigated. As a result, whereas the crystalline complex showed little change, the amorphous complex discolored yellow and developed turbidity. These results indicated that the crystalline L-carnosine zinc complex is more stable to heat and moisture than is the amorphous complex.

(12) Filtration time: Compared with the crystalline L-carnosine zinc complex, the amorphous L-carnosine zinc complex required about 3 times as long a filtration time. Thus, the crystallilne complex is remarkably superior in processability.

The novel crystalline L-carnosine zinc complex according to the invention is identifiable as a specific substance as mentioned hereinbefore, stable against heat and moisture and lean in impurity and has high antiulcer activity, indicating that it has excellent properties as a drug. Furthermore, it features a short filtration time, contributing much to productivity in commercial production.

(13) Pharmacological tests: The efficacy of the crystalline L-carnosine zinc complex was compared with that of the amorphous complex in the rat restraint water-immersion stress ulcer model and HCL-ethanol ulcer model.

Test substances

Amorphous L-carnosine zinc complex: product of Reference Example 1
Crystalline L-carnosine zinc complex: product of Example 1

Test methods

Water-immersion stress ulcer

Male Slc:SD rats aged 7 weeks were used in groups of 6–8 animals. After the animals were fasted for 24 hours, the test substances were administered orally. After 30 minutes, the animals were immobilized in water-immersion stress cages and immersed in water at 23° C. up to the xiphoid for stress loading. After 7 hours, the stomach was isolated, perfused with 10 ml of 2% formalin and fixed in the same solution. After 15 minutes, the stomach was incised along the greater curvature and the major lengths of the ulcers induced in the grandular portion of the stomach were measured under a stereoscopic microscope (magnification ×10). The total length was regarded as the ulcer index (mm).

HCl-ethanol ulcer

Male Slc:SD rats aged 6 weeks were used in groups of 6–8 animals. The animals were fasted for 24 hours and, then, the test substances were administered orally. After 30 minutes, 1 ml/rat of 150 mM HCl in 60% ethanol was further administered orally. The stomach was enucleated after 1 hour. The subsequent procedure was identical with that used in the water-immersion stress ulcer experiment.

Results

The test results are shown in Tables 1 and 2. It is apparent that the crystalline complex exhibited stronger antiulcer activity than did the amorphous complex.

TABLE 1

| | Effect against water-immersion stress ulcer | | |
|---|---|---|---|
| Sample | Dosage (mg/kg, p.o.) | Ulcer index Mean ± S.E. (mm) | % Inhibition |
| Untreated control | — | 15.6 ± 2.45 | — |
| Crystalline L-carnosine zinc complex | 100 | 0.7 ± 0.49*** | 95.7 |
| Amorphous L-carnosine zinc complex | 100 | 5.0 ± 4.61* | 68.0 |
| Cimetidine | 100 | 1.5 ± 0.56*** | 90.4 |

*; $p<0.050$
***; $p<0.001$

TABLE 2

| | Effect against HCl-ethanol ulcer | | |
|---|---|---|---|
| Sample | Dosage (mg/kg, p.o.) | Ulcer index Mean ± S.E. (mm) | % Inhibition |
| Untreated control | — | 68.4 ± 8.41 | — |
| Crystalline L-carnosine zinc complex | 10 | 7.3 ± 3.16*** | 89.3 |
| Amorphous L-carnosine zinc complex | 10 | 12.8 ± 7.48*** | 81.2 |
| Cimetidine | 30 | 71.0 ± 18.50 | −3.8 |

***; $p<0.001$

EXAMPLE 1

In 100 ml of methanol was dissolved 3.51 g of sodium hydroxide followed by addition of 9.96 g of L-carnosine to give a homogeneous solution. Then, a solution prepared by dissolving 9.67 g of zinc acetate dihydrate in 145 ml of methanol was added dropwise to the above solution over a period of 30 minutes with stirring, whereby a white precipitate was formed by degrees. After completion of dropwise addition, the reaction mixture was further stirred for 2 hours and, then, allowed to stand overnight. The resulting precipitate was collected by filtration, washed with 140 ml of water and dried in the air at 80° C. for 5 hours to recover 12.4 g of white crystalline powder. The crystalline powder was subjected to the various analyses described hereinbefore.

EXAMPLE 2

In 70 ml of acetonitrile was suspended 9.96 g of L-carnosine followed by addition of 3.52 g of sodium hydroxide. The mixture was stirred to give a homogenous solution and, then, a solution prepared by dissolving 9.67 g of zinc acetate dihydrate in 145 ml of acetonitrile was added dropwise over 30 minutes, whereby white precipitates were formed by degrees. After completion of dropwise addition, the mixture was stirred for 2 hours, allowed to stand overnight. The resulting precipitate was collected by filtration, washed with 140 ml of water and dried in the air at 80° C. for 5 hours to give 12.1 g of white crystalline powder. The IR, NMR and other physical constant of this product were in agreement with those of the product according to Example 1.

REFERENCE EXAMPLE 1

In 100 ml of water was dissolved 3.51 g of sodium hydroxide followed by addition of 9.96 g of L-carnosine with stirring to give a homogeneous solution. Then, a solution prepared by dissolving 9.67 g of zinc acetate dihydrate in 145 ml of water was added dropwise over 30 minutes. The mixture was stirred for 2 hours and allowed to stand overnight. The resulting white precipitate was collected by filtration, washed with 140 ml of water and dried in the air at 80° C. for 5 hours to give 13.2 g of white amorphous powder. This powder was subjected to the various analyses described hereinbefore. It was found that this product was an amorphous L-carnosine zinc complex differing from the products of Examples 1 and 2.

REFERENCE EXAMPLE 2

The method described by G. Weitzel et al. (Hoppe-S-Z. Physiol. Chem., 307, 23 (1957)) was followed for verification.

Thus, 5.00 g of L-carnosine was dissolved in 221 ml of water and with stirring, a solution of 2.21 g of zinc chloride in 15 ml of water was added. A small amount of 1N-HCL was added to the mixture to give a homogeneous solution, which was then cautiously adjusted to pH 7 with 0.06 N-NaOH. In the meantime, a white precipitate was formed. The reaction mixture was further stirred for 15 minutes, after which it was filtered. The precipitate was washed with 100 ml each of water, ethanol and ether in succession and dried in the air at 80° C. for 5 hours to give 2.52 g of white amorphous powder. The physical values of this powder were in good agreement with the product of Reference Example 1 and as pointed out by Weitzel in the above literature, it was an amorphous L-carnosine zinc complex.

We claim:

1. A crystalline L-carnosine zinc complex with an elemental analysis substantially corresponding to the formula $C_9H_{12}N_4O_3Zn$.

2. A pharmaceutical composition having antiulcer activity, which comprises an antiulcer-effective amount of the crystalline L-carnosine zinc complex of claim 1 and a pharmaceutically acceptable carrier.

3. A method for treating ulcers in a host which comprises administering to said host, an antiulcer effective amount of the crystalline L-carnosine zinc complex of claim 1.

* * * * *